(12) United States Patent
Anstead et al.

(10) Patent No.: US 6,939,319 B1
(45) Date of Patent: Sep. 6, 2005

(54) PROCESS AND DEVICE FOR SINGLE USE, NEEDLE-FREE INTRADERMAL, SUBCUTANEOUS, OR INTRAMUSCULAR INJECTIONS

(76) Inventors: Conrad Anstead, 31460 El Camino Real, S. Juan Capistrano, CA (US) 92675; Robert W. Brant, 88 Village St., Satellite Beach, FL (US) 32937; John M. Deslierres, 2337 E. Brookdale Pl., Fullerton, CA (US) 92831

( * ) Notice: Subject to any disclaimer, the term of this patent is extended or adjusted under 35 U.S.C. 154(b) by 192 days.

(21) Appl. No.: 10/603,496

(22) Filed: Jun. 25, 2003

Related U.S. Application Data (60) Provisional application No. 60/427,708, filed on Nov. 20, 2002, and provisional application No. 60/469,443, filed on May 9, 2003.

(51) Int. Cl.[7] .............................................. A61M 5/30
(52) U.S. Cl. .......................................... 604/68; 604/72
(58) Field of Search .................... 604/68–72, 131–136, 604/93.01, 118, 119, 140, 181, 187

(56) References Cited

U.S. PATENT DOCUMENTS

| | | | | |
|---|---|---|---|---|
| 5,062,830 A | * | 11/1991 | Dunlap | 604/68 |
| 5,911,703 A | * | 6/1999 | Slate et al. | 604/68 |
| 6,406,456 B1 | * | 6/2002 | Slate et al. | 604/68 |
| 6,652,483 B2 | * | 11/2003 | Burk et al. | 604/68 |
| 6,689,092 B2 | * | 2/2004 | Zierenberg et al. | 604/68 |
| 6,817,986 B2 | * | 11/2004 | Slate et al. | 604/68 |

* cited by examiner

*Primary Examiner*—Nicholos D. Lucchesi
*Assistant Examiner*—Matthew F DeSanto (57) ABSTRACT

A process and device for single use, needle-free hypodermic, intradermal, subcutaneous and intramuscular injections of medicament with manually or pneumatic operated injector device using vacuum to stretch and properly hold the skin for horizontally to perpendicularly delivering to a human or animal a premeasured dose of medicament or vaccine by means of a thin high pressure liquid jet stream of sufficient velocity to penetrate the epidermis of the subject and depositing the medicament in the desired depths of tissue. Utilizing disposable single use, filled or pre-filled medicament ampules, the manually operated injector device provides the interface features for mounting the ampule, and the features for supplying the impulse force required to inject the medicament upon activation and safety interlock features to prevent inadvertent activation until the ampule is properly interfaced with the epidermis. A second embodiment that functions and operates in like manner, that utilizes external air pressure for activating several injector components in lieu of the manual operations of the primary embodiment and two methods for filling the single use ampule from an external supply.

4 Claims, 8 Drawing Sheets

PROCESS AND DEVICE FOR SINGLE USE, NEEDLE-FREE INTRADERMAL, SUBCUTANEOUS, OR INTRAMUSCULAR INJECTIONS

CROSS REFERENCE TO RELATED APPLICATIONS

Provisional Patent No. 60/427,708 of Nov. 20, 2002
Provisional Patent No. 60/469,443 of May 9, 2003.

BACKGROUND OF THE INVENTION

This invention relates to the process of injecting medicament by means of a disposable, single use, filled or pre-filled, ampule utilizing an impact impulse injector that horizontally to perpendicularly delivers intradermal, (ID), subcutaneous (SUB-Q) and intramuscular (IM) injection in a human or animal tissue by means of a thin high pressure liquid jet stream of sufficient velocity to penetrate the tissue of the recipient. The injector deposits the medicament intradermally, or subcutaneously, or intramuscularly, utilizing a single use, disposable, medicament ampule that is designed to provide interfaces to the activation device, allowing easy installation by hand, and providing exact positioning and sealing to the activation device structure. The ampule further contains features that induce a vacuum to stretch the skin, keeping the skin precisely aligned with the jet orifice for the short duration of the injection. The ampule's orifice has different offset variations for ID, SUB-Q or IM injections. Ampules and injectors may also be adjusted for variations in medicament viscosity as required by various classes of medicaments. The manually operated or pneumatically activation device provides the interface features for mounting the ampule, and the features necessary for the impulse force to horizontally to vertically inject the medicament, as the activation process is performed. In addition, the activation device provides safety interlock features which prevent the impulse force from being inadvertently activated, except when the ampule is properly interfaced with the skin surface. The injector provides the operator with a comfortable, light weight device that allows the operator to quickly and easily load an ampule, properly position the ampule on the skin surface, activate the impulse force, injecting the medicament and resetting the activation device.

In this invention, a needle-free ampule discharges a pre-measured quantity of fluid medicament in a thin jet at a sufficient velocity to horizontally to vertically penetrate the tissue of both human and animal to be treated or vaccinated.

This invention utilizes a single-use, disposable medicament ampule which uses a vacuum to stretch and properly hold the skin for injecting into the tissue, and a manually or pneumatically operated activation injector device. The ampule and the injector are truly unique designs. Although they are constructed with materials presently being used in the medical industry, they were designed to minimize effort, be easy to handle and operate. The size and shape selected also minimize weight. The age, size of hands, hand strength, skin type and thickness, as well as visibility of operations, were very important considerations.

Present state of the art that attempts to inject medications intradermally have met with only limited success due to the inherent difficulty associated with accurate positioning of the skin relative to the injector jet opening and the lack of precise control of the jet pressure vs. skin penetration when the injection is performed normal to the skin surface. In addition, present systems lack precise control and repeatability of the injection jet velocity due to mechanical equipment tolerance variations within the pressure/force generators utilized. Some present devices present safety concerns due to the lack of safety interlocks to prevent the device from being activated when not in proper contact with the skin, and catastrophic failures have been observed in the injector bodies in part caused by the lack of pressure control inherent in the device designs.

Needleless injectors have been used as an alternative to hypodermic needle type injectors for delivering drugs, vaccines, local anaesthetics and other fluids into the human or animal tissue. The medicament is discharged in at high velocity after first penetrating the epidermis and thereafter be deposited in the tissues of the subject. An alternative method is to press the discharge nozzle onto the skin and force the fluid at very high pressure through the epidermis.

Prior art devices generally employ spring loaded piston pumps to generate injection pressure to withdraw fluid from a reservoir. At the end of the piston stroke, the piston is disengaged from the retracting mechanism and pressures the fluid from the delivery nozzle. In some devices the fluid is contained in an adjacent container or vessel within the device and the fluid is fed into the nozzle under pressure and discharged under pressure by the delivery nozzle, In other prior art devices the piston is driven on the discharge stroke by gas or electric motor instead of a spring. In most of these devices the discharge orifice is placed firmly on the skin to make contact of the nozzle to the epidermis, and to achieve suitable contact, the orifice is pressed firmly into the epidermis normal to the surface. This is done to stretch the epidermis at point of contact and increase the ability of the injection to penetrate the stretched tissue at point of contact. However, the pressing of the orifice into the epidermis is a variable dependent on the device's operator, and the ability of the recipients to tolerate the device being pressed against their anatomy.

Typically, the use of existing devices results in loss of medicament at the nozzle entry point, poor injections on account of recipient's movements, and receipt of the injection at an angle that does not penetrate or penetrates too much for placement and dispersal of the medicament at the correct depth and layer of tissue. In addition, premature operations are common, as well as relative movement between the epidermis and orifice can cause tearing of the skin during injection, resulting in pain and poor transfer of the medicament to the recipient. In other instances, the epidermis will deform away from the orifice and the injection fluid will leak away from the point of entry. At other times, the devices attempt to stretch the epidermis by deforming over the discharge orifice. In all of these conditions, the success of the injection procedure depends and rests on the ability of the applier to consistently perform, using the device to get an acceptable discharge and penetration of the epidermis.

Various methods have been proposed to overcome these problems such as powered injectors, sensing and control devices to enhance their performance, including compressed gas cylinder and electrical injectors, often heavy and unwieldy, and encombered with variations in gas supply, pressure, leakage.

The need for medicament supply and personnel skill have produced a problem for using these devices, precisely measuring and control of the quantity of medicament administered and ensuring that the injector delivers the correct amount of medicament into the proper tissue.

The following patents addressed these known problems and proposed some methods, as follows:

U.S. Pat. No. 3,859,996, Mizzy, discloses a controlled leak method to ensure that the injector orifice is placed correctly at the required pressure on the subject's skin at the corrrect normal to the skin attitude. When placement conditions are met, controlled leak is sealed off by contact pressure on the subject's skin, the pressure within the injector control circuit rises until a pressure sensitive pilot valve opens to admit high pressure gas to drive the piston and inject the medicament. This use of valving and pressure gas does not apply to the present invention.

WO Patent 82/02835. Cohen and Ep-A-347190, Finger, discloses a method to improve the seal between the orifice and the skin and prevent relative movement between each. This method is to employ a vacuum device to suck the epidermis directly and firmly onto the discharge orifice. The discharge orifice is positioned normal to the skin surface in order to suck the epidermis into the orifice. This method for injection of the medicament into the skin and the injector mechanism are different and do not apply to the present invention because of its unique ampule design.

U.S. Pat. No. 3,859,996, Mizzy, discloses a pressure sensitive sleeve on the injector which is placed on the subject, whereby operation of the injector is prevented from operating until the correct contact pressure between orifice and the skin is achieved. The basic aim is to stretch the epidermis over the discharge orifice and apply the pressurized medicament at a rate which is higher than the epidermis will deform away from the orifice. This method of stretching the skin on to the orifice, together with the arrangements of the mechanism are totally different from the present invention and, consequently, do not apply.

U.S. Pat. No. 5,480,381, T. Weston, discloses a means of pressuring the medicament at a sufficiently high rate to pierce the epidermis before it has time to deform away from the orifice. In addition, the device directly senses that the pressure of the discharge orifice on the subject's epidermis is at a predetermined value to permit operation of the injector. The device is based on a cam and cam follower mechanism for mechanical sequencing, and contains a chamber provided with a liquid outlet for expelling the liquid, and an impact member, to dispell the liquid. The sequencing and cam operation driven by an electric motor gear-box, cam action sequencing and adjustable pressure sensing do not apply to the present invention.

U.S. Pat. No. 5,891,086, T. Weston, describes a needleless injector that contains a chamber that is pre-filled with a pressurized gas which exerts a constant force on an impact member in order to strike components of a cartridge and expulse a dose of medicament. This device contains an adjustment knob which sets the dose and the impact gap, and uses direct contact pressure sensing to initiate the injection. This use of contact pressure sensing, the need for constant adjustment and the use of pressurized gas to implement the injection process do not apply to the present invention.

BRIEF SUMMARY OF THE INVENTION

The subject of the present invention represents an innovative approach to hypodermic needle-free injections, either Intradermal (ID), Subcutaneous (SUB-Q) or Intramuscular (IM), providing a process and a mechanization which contains disposable filled or prefilled medicament ampules and a manually operated activation device. There are many advantages covered by this invention. Above all, the injection uses horizontal impact impulse jet pressure, and thus it spreads the particles over a larger area than using a needle syringe, decreases the local pressure in the tissue, and eliminates leakage of the fluid from the opening in the tissue, and this reduces possibility of spreading infections. Some other angles may be chosen for injection position, besides the horizontal one, depending on specific conditions. The major unique feature of this invention is that the medicament is driven out of the ampule that holds it with a known controlled impact impulse force.

The next important innovation of the present invention is the process of the stretching of the skin, which increases permeability thus reducing the amount of energy required to inject fluid into a tissue, in conjunction with the injecting of the fluid horizontally to vertically into the skin which allows controlled positioning of the tissue for intradermal, subcutaneous or intramuscular injections. Significant is also the introduction of a safety feature built into the injector that will not allow operation until the skin is properly positioned.

The ampule interfaces with the activation device allowing installation by hand or machine fixture, and has features for the use of a vacuum that stretches and properly holds the skin, precisely aligned with the jet orifice during the short duration of the horizontal injection. The activation device provides the interface for mounting the ampule and for delivering the impact impulse force required to inject the medicament as the activation process is performed. When filling ampules, each ampule body contains a see through window with external gradient markers to indicate quantity of medicament the ampule contains.

In a second embodiment of this invention, the injector operates in like manner as the primary embodiment, with the exception that certain functions and sequence operating components utilize external air pressure for activation. The handle has been replaced with a finger operated trigger, and return functions are all air driven. The ampule configuration in both embodiments is identical and its attachment to the injector and filling procedure the same. Inasmuch as each ejector embodiment utilizes the same ampule, then each provides a means for administering either Intradermal (ID), Subcutaneous (SUB-Q) or Intramuscular (IM) injections.

Present state of the art attempts to inject medications intradermally have met with only limited success due to the inherent difficulty associated with accurate positioning of the skin relative to the injector jet opening and the lack of precise control of the jet pressure versus skin penetration when the injection is performed normal to the skin surface. In addition, present systems lack precise control and repeatability of the injection jet velocity due to mechanical equipment tolerance variations within the pressure/force generators utilized. Some present devices indicate safety concerns due to the lack of safety interlocks to prevent the device from being accidentally activated when not in proper contact with the skin, and observed catastrophic failures in the injector bodies in part caused by the lack of precise pressure control inherent in the device designs.

Although the injector does not touch the skin tissue around the injection, it can be submerged in alcohol for sterilization, if desired, since all materials are presently being used in the medical industry, and are compatible with all current sterilization methods.

BRIEF DESCRIPTION OF THE SEVERAL VIEWS OF THE DRAWINGS

FIG. 3 shows a cross section view of the injector 20 prior to activation of the injection process. The injector is comprised of the housing for a piston 35 to create a vacuum for stretching the recipient's skin on injection application, and for the release mechanism to pressure drive the medicament into the skin tissue. The housing of the injector contains a compression drive spring 42 that drives the end of the drive rod 43 into the ampule 25 that contains the medicament, and the drive rod 43 contains a retention ring 59, at the opposite end, that is used for locking the drive rod with the compression spring compressed, and a projecting ring 120 for the compression spring to push against. To eject the medicament 31 out of the ampule, rotation of the handle 30 pushes a slide frame 45, with an extension link 40, that compresses the compression drive spring 42, by using a drive rod latch 48 that snares the retention ring 59, that forms a portion of said drive spring drive rod 43. As the slide frame 45 is pulled in one direction by the link 40, attached to the handle, the latch 48 is rotated down behind the retention ring 59 and engages it. The drive rod latch for capture of the drive rod 43, with the compression spring compressed, is pre-loaded to the release position by a torsion spring 53, that is driven down against the torsion spring load to a locking position that captures the drive rod retention ring 59, and the drive rod latch is driven down against the torsion spring load with a spring ramp 50, retained by two pins 51, in the housing. The drive rod latch is supported by the slide frame 45, and can rotate around a pin joint 52 in the upright supports of the slide frame, and is retained in the slide frame with a horizontal pin 58, that also retains a connector link 47. The slide frame has a horizontal lower leg that slides in and is guided by a machined-in groove, in the housing 21, and the horizontal lower leg contains an end termination pivot point 60 for attachment of an extension link 40, that can rotate. The rotation of the handle 30, back to the starting position, pulls on the drive rod 45, and compresses the spring and holds it in a compressed position ready for release to drive the medicament 31 out of the ampule with the drive rod 43. To achieve this movement of the slide frame 45, with the link 40, that is attached to both slide frame and handle, the link rotates around a pivot 41, on the handle, and a pivot 60, on the slide frame. In addition, the handle 30, is attached to the injector assembly housing 21, and rotates around the pivot 24. The injector handle 30, attached to the outside of the housing contains two contoured legs that straddle the housing, and each leg is attached to the pivot point 24 in the housing structure. The injector handle contains a shape that is formed or molded to provide finger or hand grip 29, can rotate around the pivot point 24 in the housing structure, and is retained in the pivot point by the capture pin 58. The handle is of extended length in order to provide sufficient leverage for compressing the drive rod compression spring 42. It contains an extension link, and can rotate around its handle attachment point permitting the extension link 40 to rotate when the handle is also rotated, and is attached to the slide frame 45, it pivots about the pin joint 60 at the opposite end from the handle, so that when the handle is rotated down, or up, the extension link pushes or pulls on the slide frame. The slide frame 45 is also utilized for a separate function. To ensure good contact of the ampule 25 with the skin of the recipient, during the medicament injection, the injector creates a vacuum at this contact point with the ampule 25 and the recipient's skin. To achieve this vacuum the slide frame 45 has attached to it a connector link 47 that engages a vacuum piston 35, for creation of the vacuum at the skin upon the ampule contact. The slide frame 45 movement, in one direction, compresses the compression spring 42 and pulls the drive rod 43 to the latched loaded position, with said connector link 47, attached to the upright supports of the slide frame, at one end, and on the opposite end, attached to the piston extension 46, with a rod latch pivot pin 54. The piston provides the vacuum for the injector 20, when applied to the recipient's skin, to pull and stretch the skin tight against the suction ports 63, in the ampule 25, and position the outlet orifice 66 correctly for injection of the medicament, and provides the vacuum seal to the ampule with the skin as a safety device to prevent inadvertent triggering of the injector 20 with the use of a vacuum, for movement of a small interlock piston rod 36, to engage or disengage a release catch 44. The piston 35 contains an O-ring seal 34, that ensures that the piston can produce a vacuum for actuation of the small interlock piston rod 36, and ensures that the vacuum provided will position the small interlock piston rod to engage the release arm 55, and either lock it in non-release, or release position, and the release arm 55 is torsion spring 33, loaded to the lock position, and able to rotate to the two operating positions around a pivot pin 54 that interfaces with the injector housing structure.

Figure 1:
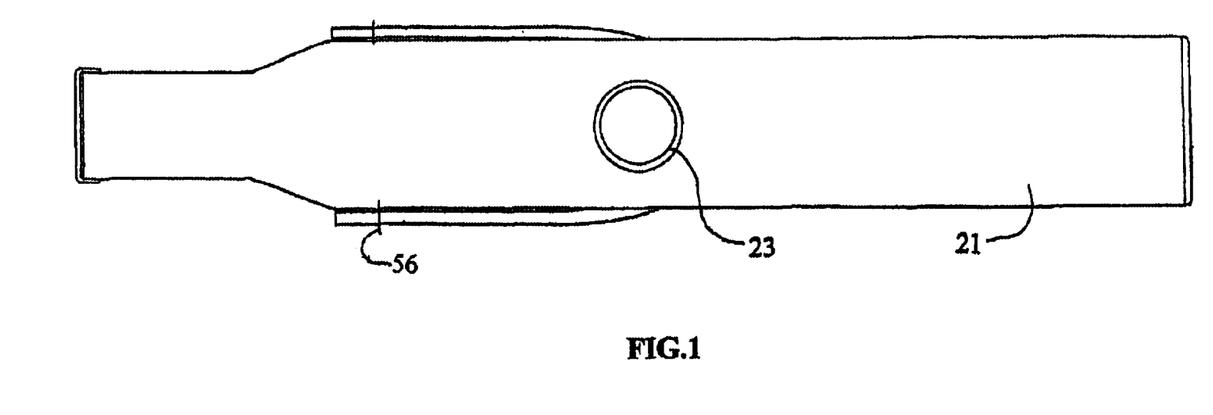
FIG. 1—Top View of Needle-Free Injector
Figure 2:
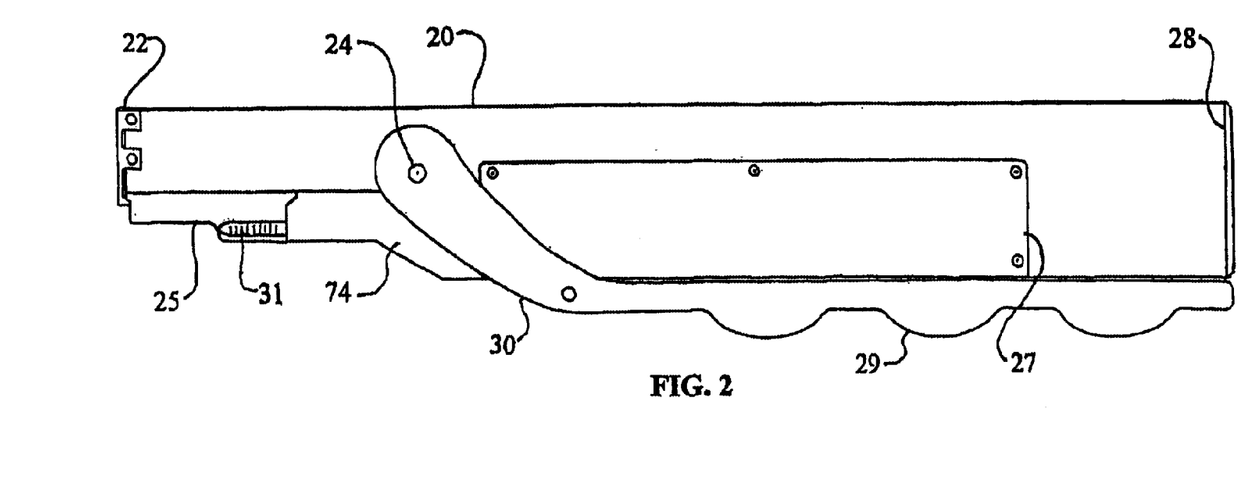
FIG. 2—Side View of Needle-Free Injector Manual Configuration
Figure 3:
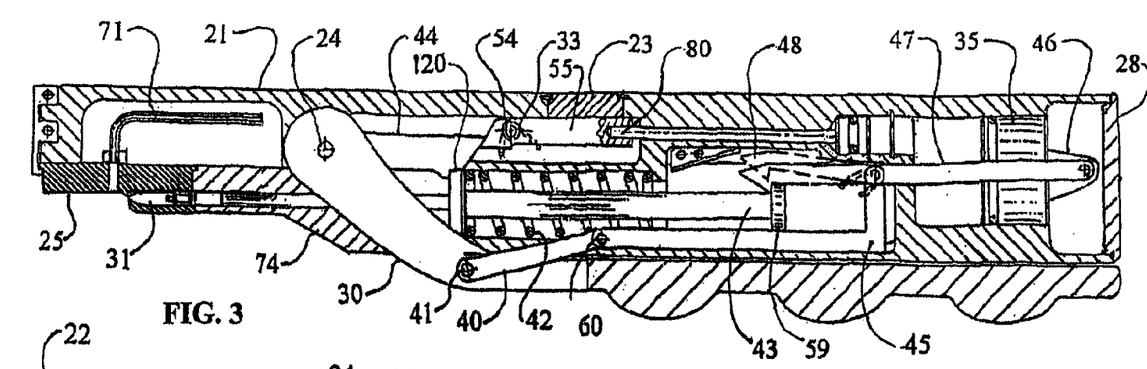
FIG. 3—Cross Section View of Needle-Free Injector Prior to Inject
Figure 4:
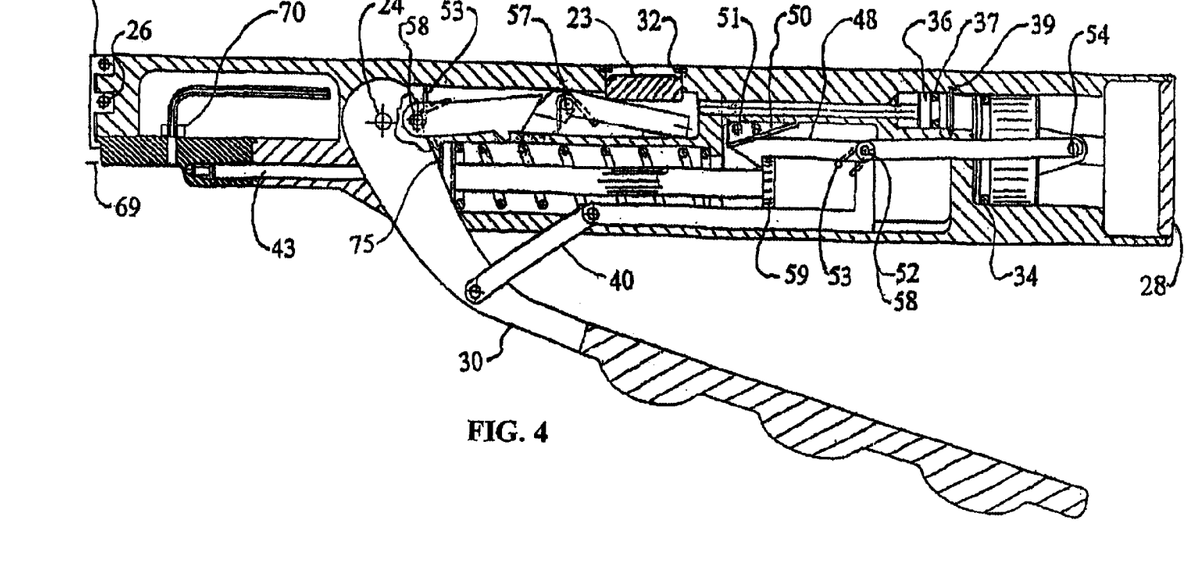
FIG. 4—Cross Section of Needle-Free Injector After Injection
Figure 5:
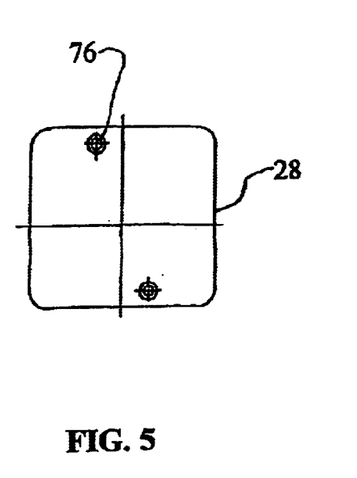
FIG. 5—End Cap of Needle-Free Injector
Figure 6:
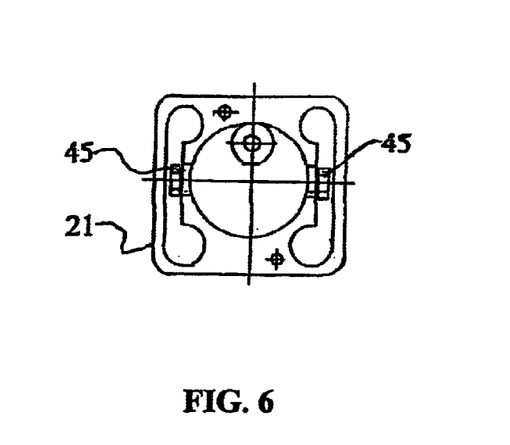
FIG. 6—Cross Section Through Injector at Vacuum Piston
Figure 7:
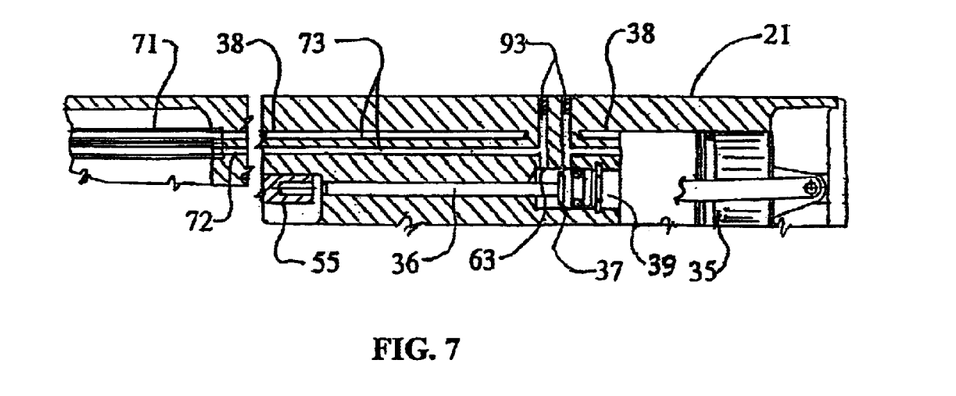
FIG. 7—Cross Section Through Suction Manifold

A pair of connector links 47 straddle the vacuum piston 35 and are connected to it with the piston extension 46. Movement of the slide frame 45 drives the vacuum piston 35, and the vacuum created is ported to the ampule 25 through a suction tube 71. To release the drive rod 43, the injector contains a release button 23 that, when pressed by the injector holder's finger, rotates the release arm 55, that holds the release catch 44, and in turn prevents the spring 42 from driving the drive rod 43 into the ampule. The release arm, that engages the release catch 44 rotates around the engagement pin 54, and the torsion spring 33 engages and holds the release arm 55 in lock position. The release button 23 is installed in the injector housing 21 structure, so that when pushed inward contacts the release arm 55, and rotates it downward to, in turn, lift the release catch 43, that locks the compression spring in its loaded compression position, and the release button 23 is retained in the injector housing structure flush with the structure's outer surface to prevent operators from inadvertently pushing of the button down, until required by the operating procedure, and is retained in the housing structure with a retention snap ring 32. The release catch 44 contains the torsion spring 53, that drives it into the lock position to hold the drive rod 43 against the compressed compression spring 42, and contains an angular surface that provides a means for contact with the release arm 55, during release function, and the release catch 44 is pivoted around the pivot point provided by the latch pin 58 that engages the housing 21 structure. FIG. 4 shows a cross section view of the injector 20 after injection of the medicament, and with the handle 30 rotated away from the housing. To ensure that the drive rod latch 48 always engages, the drive rod retention ring 59, a spring ramp 50 forces the drive rod latch down to engage and lock on to the projecting retention ring 59. The spring ramp is retained by two roll pins 51. To ensure that the drive rod latch 48 releases at the end of the slide frame 45 travel, the latch 48 contains the torsion spring 53 that is retained by the pin 58, and drives the latch to the release position around pivot pin 52. To achieve the vacuum, piston 35 contains an O-ring seal 34 that creates the vacuum at the ampule. The vacuum tube 71 contains a seal 70, at the point of interface with the ampule, to ensure the function of suction of the skin at ampule contact, for efficient injection of the medicament by the injector. The injection release button's 23 lower surface, when pressed, cams down the release arm 55 and forces up the release catch 44. The release arm rotates around a pivot point 57 that holds the pin 54 and torsion spring 33. To ensure that the release arm cannot accidently be rotated by someone pressing on the button before it is needed, and to ensure that the recipient's skin is in contact with the ampule 25, ready for injection, the injector 20 contains a locking feature that prevents the possible release of the drive rod 43. When the handle 30 is rotated, and vacuum is created by movement of the slide frame 45, and resultant movement of the vacuum piston 35, the suction created also is used to move the interlock piston rod 36 that engages the release arm 55. Until there is full suction on the system, the piston rod is interlocked with the release arm that contains a mating interlock hole 80, and no medicament can be ejected. The interlock piston rod 36 contains an O-ring 37 to maintain the vacuum between large piston 35 and the interlock piston rod 36. In the space between the two sealed pistons there is a suction port A 38, shown in FIG. 7, for the transfer of vaccum to the ampule. To prevent the interlock piston rod 36 from overtraveling, and to hold it in its correct position for activation by the vacuum, the interlock piston rod is retained with a retainer ring 39. To ensure that the large drive compression spring does not drive the drive rod hard against an end stop, and does not damage the ampule 25, the drive rod bottoms out on a cushion washer 75, when released. FIG. 4 also indicates the surface 69 that contacts the recipient's skin for injection of the medicament. The ampule 25 is expendable and can be easily installed on the ejector assembly by rotating the retainer clamp 22 that is detented 26, on to the housing 21 of the injector assembly. FIG. 5 shows an end view of the injector assembly and end cap 28, with its attachment screws 76. FIG. 6 provides a cross section view of said housing 21, and indicates the two legs of the slide frame 45 as they straddle the vacuum piston 35. FIG. 7 provides a sectional view through the housing, and shows the routing and passages through the suction manifold 72. The manifold suction passages 73 supply the necessary vacuum for extracting the interlock piston rod 36 from release arm 55 with said small incoming vacuum for movement of the piston rod into the injector assembly 20. The suction manifold system is comprised of machined vacuum ports in the housing structure to receive the vacuum pressure from the vacuum piston 35 and conduct a vacuum through ported suction passages 73, in the structure, within the vacuum piston chamber, to the interlock piston chamber, and to the suction tubes 71, that interface with the ampule, and the suction passages are sequentially opened and closed by positioning of the interlock piston 36, and a pair of suction tubes that conduct the suction from the machined-in structure suction passages to the suction ports 63 in the ampule 25.

Figure 8:
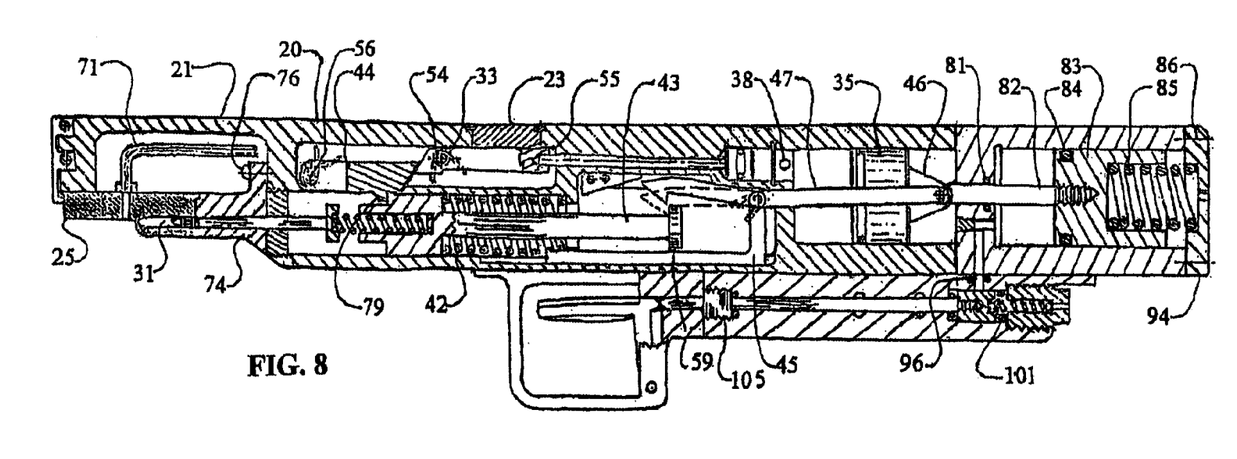
FIG. 8—Cross Section View of Injector, Air Pressure Configuration
Figure 9:
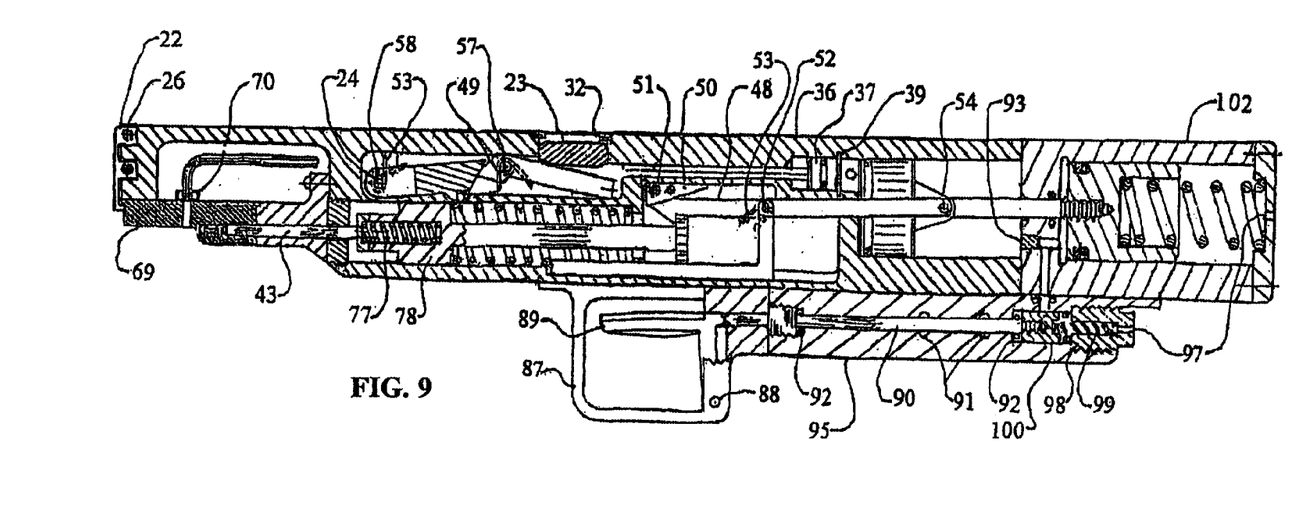
FIG. 9—Cross Section View of Injector after Injection
Figures 10A, 10B:
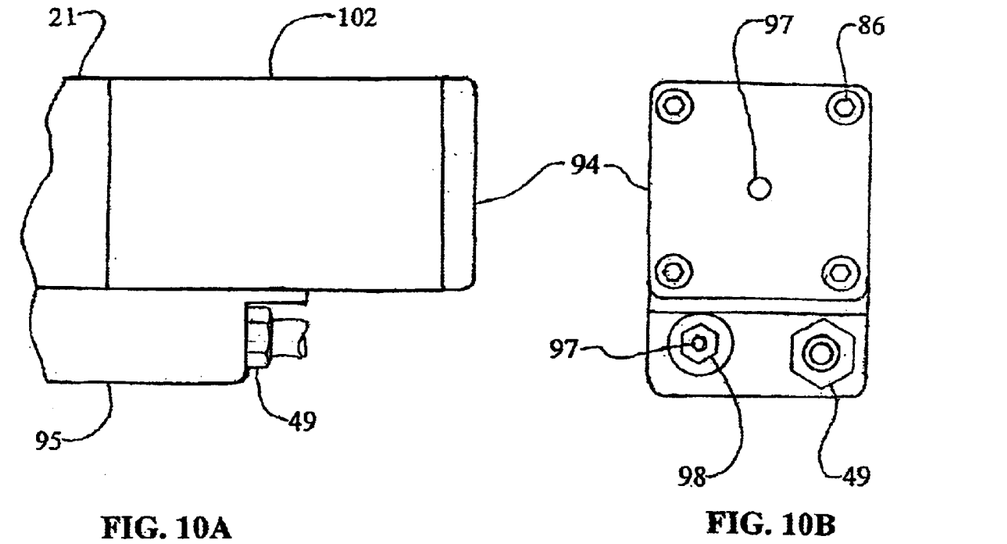
FIG. 10—View Showing Air Supply Connection and Manifold
Figure 11:
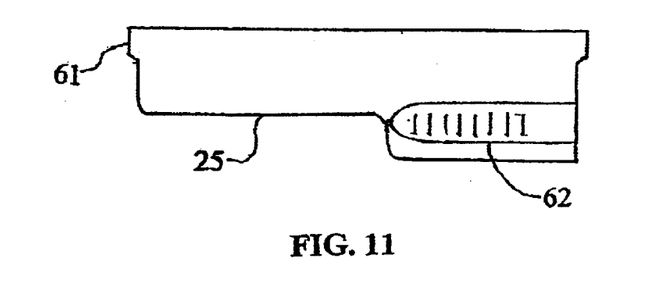
FIG. 11—Exterior View of Ampule
Figure 12:
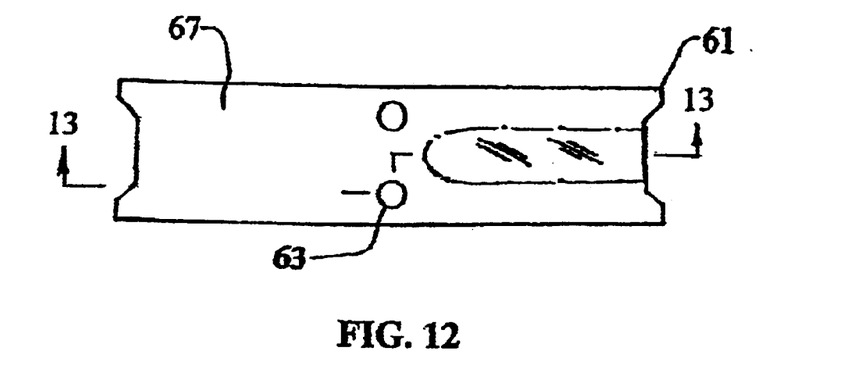
FIG. 12—Top View of Ampule
Figure 13:
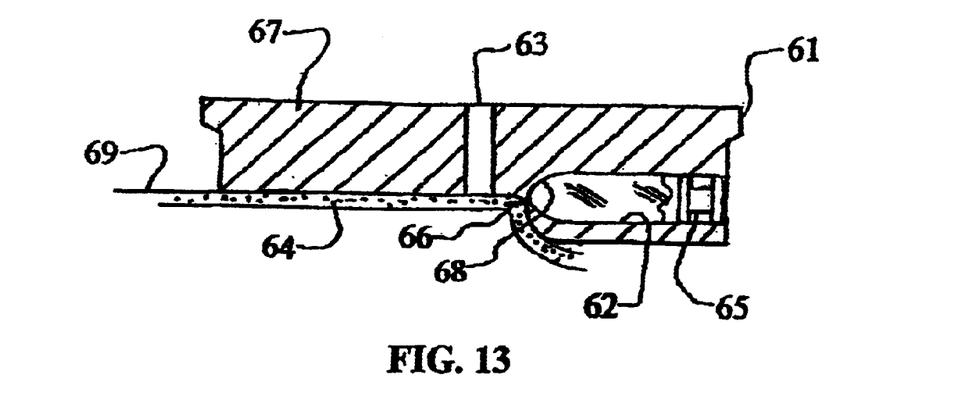
FIG. 13—Cross Section Through Ampule
Figure 14:
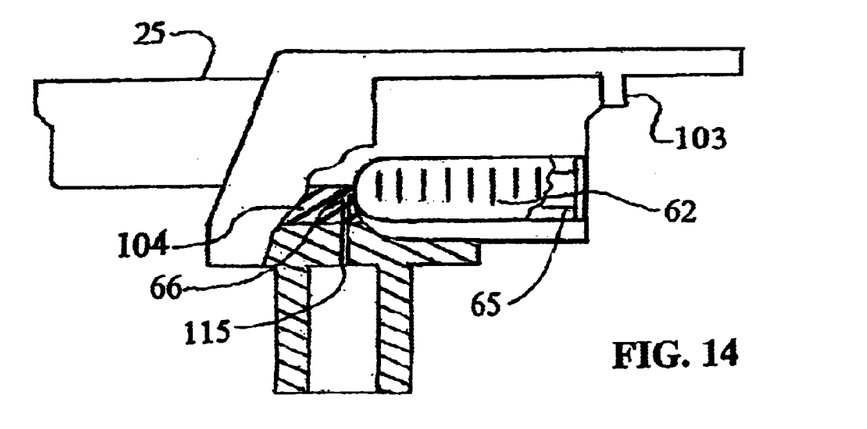
FIG. 14—Ampule Adaptor for Filling
Figure 15:
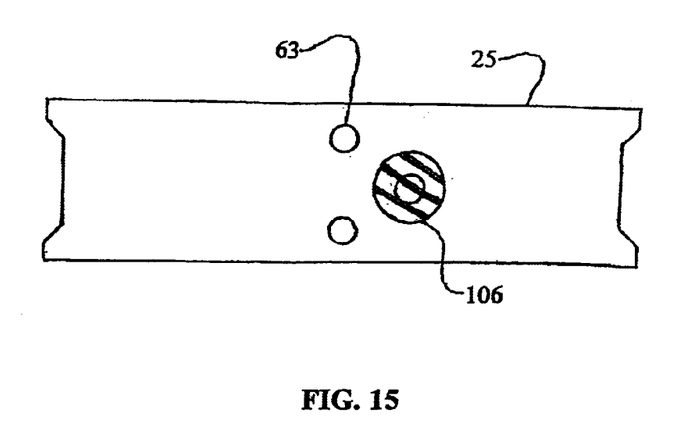
FIG. 15—Top View of Ampule Showing Stopper for Filling
Figure 16:
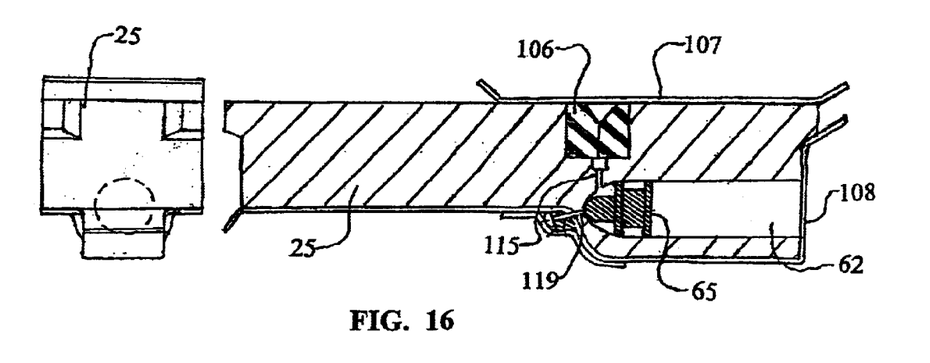
FIG. 16—Sectional View with Protective Covering Ready To Be Removed and Ampule Filling Initiated FIG. 17—Cross Section View of Ampule with Syringe Ready for Air Evacuation and Medicament Filling FIG. 18—Ampule Filled with Medicament and Sealed for Use The injector assembly 20 is provided with an access panel 27 and an end cap 28 for ease of assembly and service of the housing.
Figure 17:
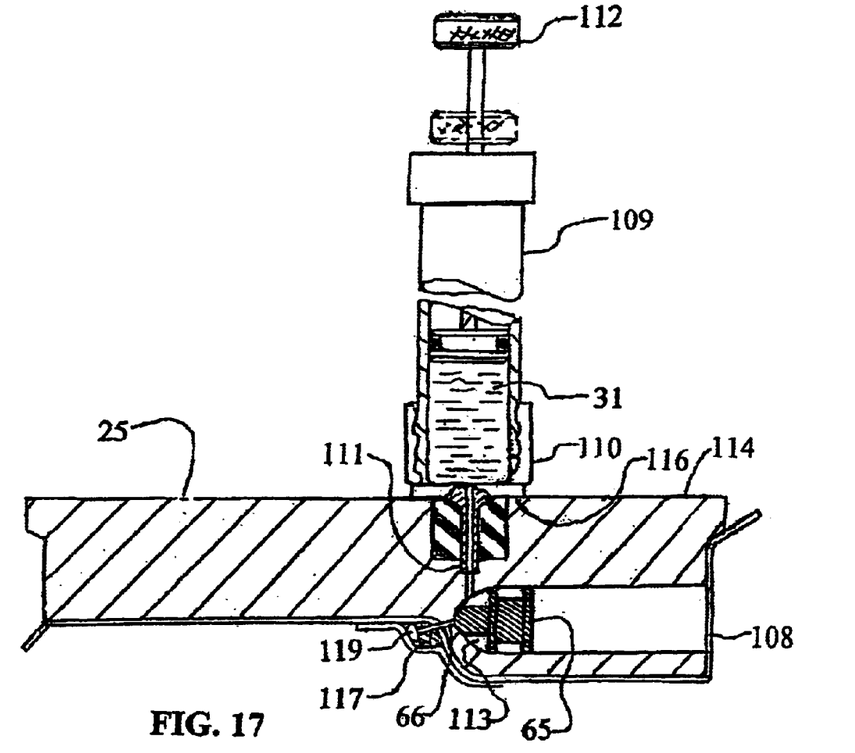
Figure 18:
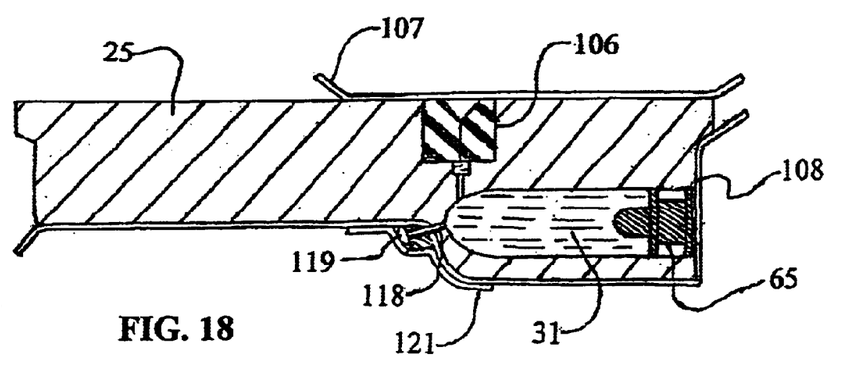

A second embodiment of the injector assembly is shown in FIG. 8 in cross section. For convenience and to avoid confusion, like parts are given the same reference numerals throughout where their function and operation are duplicated or repeated. The major difference between the two embodiments is that the former embodiment utilizes manual operation by the rotation of a hand operated handle 30, while this embodiment utilizes external air supplied power for some of its functions. In the primary embodiment manual extending downward and retracting of the handle to its initial position actuates a large piston 35 to create a vacuum that is utilized for ensuring that the recipient's skin is in direct contact with the injector's injection orifice 66. It also provides a means for preventing accidental activation of the injector and provides a means for compressing the impulse drive spring 42 to a lock position, ready for release by the operator pushing downward on the activation button 23. In this second embodiment of the invention, the external source of pressure provides a means for assisting the injector to create the necessary vacuum to achieve these same features and advantages. The vacuum assist is achieved by the operation of a valve 100 that is controlled by a trigger assembly 89. Movement of the trigger one way, opens the valve for pressure to travel tip to a large return piston 83, that pulls back on the vacuum piston 35 to create a vacuum, and initiate the same functions achieved by the previous handle movement. Activation of the trigger in opposite direction closes off the outside pressure source and, in turn, shuts down the vacuum assist function provided by the return piston 83. FIG. 8 and FIG. 9 show this new embodiment in two positions during the injection operation. This embodiment of the needle-free jet injector utilizes external air pressure for activating and sequencing the injector components. The injector contains a trigger assembly 89 that is operated by the operator's finger for initiation and movement of a valve 100 in the injector, that opens and blocks externally supplied air pressure from exterior source 49 to a large return piston 83, that is connected to the vacuum piston 35, with a connecting rod 82. The vacuum piston provides the vacuum for interlock functions of the release button, and the release catch to initiate injection of the medicament, and the vacuum piston is moved by the return piston 83 to create a vacuum at the interface contact surface of the recipient's skin and the ampule containing the medicament. The trigger assembly 89 is operated by the injector operator's finger applying a squeezing motion to move said trigger upward, toward the injector activation frame 87 and causes the trigger assembly 89 to push against a push rod 90 that operates as a valve to sequence air pressure to enter the injector from the outside air supply source 49. The push rod 90 travels fore and aft in a machined support fitting 95, that is attached to the underside of the injector assembly, and is retained within the support fitting 95 by a threaded bushing 105, that provides a means for sealing and retention of the air pressure within the support fitting. An O-ring seal 92 is captured between the bushing and the support fitting, and seals around the push rod that passes through the bushing and contacts the trigger assembly. A like O-ring seal 92 seals around the shaft and seals against the support fitting 95, and the valve 100, that is used to sequence the incoming air pressure that enters the valve cavity, through two cross pressure ports 91, from the air supply. The valve 100 blocks and opens passage for the incoming pressure to travel into the injector assembly. The valve seals against an O-ring 101, in one direction, and seals against the previous O-ring 92, in the opposite direction. The push rod 90 is machined with an undercut to permit air to travel to the valve, which than can allow it to pass up into the injector, or to be blocked by the valve and its seal. The position of the valve is controlled by the position it is put in by the trigger assembly 89. When the trigger assembly is not activated, the valve is positioned in the air blocked, closed location, by a compression spring 99, that is captured by a spring retention plug 98, that is threaded into the support fitting 95. When the valve is in the blocked, closed location, any air pressure captured in the injection, on the opposite side of the valve, is bled out of the return spring cavity though a pressure bleed hole 97. An O-ring seal 96 is installed at the interface air passage joint between the support fitting 95 and an extension housing 102, attached to the injector assembly. The air passage is used to provide pressure to drive a large return piston 83 that is connected to the vacuum piston 35, with a connecting rod 82. Air pressure behind the return piston pulls on the connecting rod, and in turn moves the slide frame 45 to accomplish what the handle enacted within the prior injector assembly. The return piston contains an O-ring 84 for piston sealing, and a compression spring 85 for the return function of the return piston. The compression spring is captured in a pocket in the return piston, and in a pocket in the spring retention cap 94. Air captured between the retention cap and the return piston is bled out of the cavity through a bleed hole 97. The retention cap 94 is attached to the extension housing 102 with retention screws 86. The air pressure into the pressure side of the return piston enters through a port machined in the extension housing 102, with the use of a passage plug 93, for changing passage direction to enter this cavity. The extension housing 102 contains an O-ring seal 81 for sealing pressure around connection rod 82. To ensure that drive rod 43, driven by the large drive spring 42, does not impact the ampule plunger 65, and causes a problem on injection of the fluid, a small compressing spring 77 is installed between the drive rod 43 and the drive cylinder 78. This compressing spring ensures that the end of the drive rod is in constant contact with the ampule plunger 65, and does not cause a condition of impact when the injector is initiated, and the release catch 44 is rotated to release position, and the tooth release catch 79 disengages with the drive cylinder 78. The result is that the medicament fluid is driven out of the ampule with high energy force supplied by the large drive spring 42. FIG. 10 provides a view showing the connection of the external air supply to the injector and the related manifolding of air passages in the injector.

The disposable filled ampule shown in FIG. 11 side view, contains the medicament and is attached to the injector and contacts the vacuum tubes, and whose body 67 is comprised of plastic, glass or equivalent material, and that is provided with a cylindrical or other shape bore chamber, for containing the medicament having an internal ampule plunger seal 65, that captures the medicament inside its chamber.

FIG. 12 shows a plan view of the ampule with suction ports 63. The ampule whose chamber is provided with gradient dosage markers 62 on the exterior surface to indicate the quantity of the medicament within, and FIG. 13 shows a section view of the chamber contoured 68 on its inner surface and contains a precision contoured throat to aid in acceleration of the medicament by reduction of the fluid drag when the ampule receives an impact impulse from the spring loaded drive rod 43, and increases the acceleration of the piston which results in a faster pressure rise and injection of the medicament. Therefore, the medicament 31 is driven out of the ampule with a known controlled impact impulse force.

The ampule, FIG. 13 section view, contains an outlet orifice 66 that is varied in location by varying the distance between the center line of the orifice and the vacuum port plane 69, and can contain interdermal, subcutaneous or intramuscular injection medicaments, and horizontally, or at any variation of angle, inject them through human or animal skin to predetermined depths in the skin layer 64, by controlling the dispersement of the medicament in injections using variation of the angle between perpendicular to the orifice and the vacuum port level plane. The ampule 25 contains locking tabs 61, on each end, for engagement with the injector, shown in FIG. 12 and FIG. 13. In order to be correctly positioned and retained in the injector, for engagement with the vacuum suction tubes 71, the interface surface is sealed with suction tubes that engage recipient's skin, and stretches the skin between ports 63 for the medicament injection into recipient's skin 64.

The ampule has provisions for filling with medicament 31 from an external supply, by either use of an adaptor assembly 103, shown in FIG. 14, that holds the ampule and seals it for filling the medicament through a rubber seal 104, in the adaptor, and permits filling of ampule through its orifice.

An optional filling method for filling medicament is through a rubber or equivalent stopper 106, shown in FIG. 15, plan view.

FIG. 16, section view, shows provisions for insertion of a probe 111 on a nozzel that penetrates the stopper, in the ampule, and whose nozzel contains a shoulder stop 116, that bears on the ampules flat surface 114, and automatically locates the probe correctly for the medicament filling shown in FIG. 17. Air must first be evacuated from the ampule air passage 115, and air space 113 within the ampule. This is accomplished with the use of syringe 109 and its retraction handle 112, prior to filling the ampule with the medicament. Removal of the probe seals off the passage containing the vacuum, and then reinserting the probe, on the nozzel, through, the stopper, fills the ampule with prescribed medicament after air evacuation.

FIG. 18 shows a means for plugging of the ampule orifice with a plug 118 when filling the medicament, and the plug contains an enlarged head 119 for ease of installation and removal, with a capture pad 117, to prevent it from being sucked into the orifice 66, and a means to prevent it from being driven out of that orifice, with the use of a protective outer doubler covering 121, and all other openings are protected with coverings, 107 and 108, in the ampule, to maintain full sterile conditions within the ampule, and provide for removal and disposal of the ampule orifice plug, with the disposed protective shield that contains a tab for easier removal of the shields from the ampule.

LIST OF PARTS AND IDENTIFACTION NUMBERS

| | |
|---|---|
| 20 | Injector Assembly (complete) |
| 21 | Housing |
| 22 | Retainer Clamp |
| 23 | Release Button |
| 24 | Pivot (Handle) |
| 25 | Ampule |
| 26 | Detent |
| 27 | Access Panel |
| 28 | End Cap |
| 29 | Hand Grips |
| 30 | Handle |
| 31 | Medicament |
| 32 | Snap Ring |
| 33 | Torsion Spring |
| 34 | Seal (Large Piston) |
| 35 | Vacuum Piston |
| 36 | Interlock Piston Rod |
| 37 | O-Ring |
| 38 | Suction Port A |
| 39 | Retainer Ring (Small Piston) |
| 40 | Extension Link |
| 41 | Pivot (Link) |
| 42 | Drive Spring |
| 43 | Drive Rod |
| 44 | Release Catch |
| 45 | Slide Frame |
| 46 | Extension (Piston) |
| 47 | Connector Link |
| 48 | Drive Rod Latch |
| 49 | External Air Source |
| 50 | Ramp |
| 51 | Roll Pins |
| 52 | Pivot (Rod Latch) |
| 53 | Torsion Spring (Rod Latch) |
| 54 | Pin |
| 55 | Release Arm |
| 56 | Shaft |
| 57 | Pivot (Release) |
| 58 | Pin (Latch) |
| 59 | Retention Ring |
| 60 | Pivot (Slide) |
| 61 | Locking Tabs |
| 62 | Cylinder Bore (with dosage markers) |
| 63 | Vacuum Ports |
| 64 | Skin |
| 65 | Ampule Plunger |
| 66 | Outlet Orifice |
| 67 | Body (Ampule) |
| 68 | Contour |
| 69 | Vacuum Port Plane |
| 70 | Seal (Vacuum Port) |
| 71 | Suction Tube |
| 72 | Suction Manifold |
| 73 | Suction Passage |
| 74 | Insert Fairing |
| 75 | Washer, Cushion |
| 76 | Screw |
| 77 | Compressing Spring |
| 78 | Drive Cylinder |
| 79 | Tooth Release Catch |
| 80 | Interlock Hole |
| 81 | O-Ring |
| 82 | Connecting Rod |
| 83 | Return Piston |
| 84 | O-Ring |
| 85 | Compression Spring |
| 86 | Retention Screws |
| 87 | Actuation Frame |
| 88 | Pin |
| 89 | Trigger Assembly |
| 90 | Push Rod |
| 91 | Pressure Ports |
| 92 | O-Ring |
| 93 | Plug |
| 94 | Spring Retention Cap |
| 95 | Support Fitting |
| 96 | O-Ring |
| 97 | Pressure Bleed |
| 98 | Spring Retention Plug |
| 99 | Spring Compression |
| 100 | Valve |
| 101 | O-Ring |
| 102 | Housing |
| 103 | Adaptor |
| 104 | Rubber Seal |
| 105 | Bushing |
| 106 | Stopper |
| 107 | Pull-off Protection Shield (upper) |
| 108 | Pull-off Protection Shield (lower) |
| 109 | Syringe |
| 110 | Nozzle |
| 111 | Probe |
| 112 | Retraction Handle |
| 113 | Vacuum Space |
| 114 | Flat Surface |
| 115 | Passage |
| 116 | Shoulder Stop |
| 117 | Capture Pad |
| 118 | Ampule Orifice Plug |
| 119 | Enlarged Head |
| 120 | Projecting Ring |
| 121 | Protective Outer Doubler |

We claim:

1. An injector comprised of a housing that contains a piston to create said vacuum for stretching the recipient's skin on injection application and for the release mechanism that drives said medicament into the skin tissue, (a) said housing of said injector comprising a compression drive spring that drives the drive rod into said ampule containing medicament, and said rod contains a retention ring used for locking said rod with said spring compressed, and a projecting ring for the spring to push against, (b) said housing contains a drive rod latch for capture of said rod with said spring compressed, and is preloaded to the release position by a torsion spring driven down to a locking position that captures said rod projecting ring, and said drive rod latch is driven down against said spring load with a spring ramp retained by two pins, (c) said drive rod latch is supported by a slide frame and can rotate in the upright supports of said frame, and retained with a horizontal pin that retains a connector link, and said slide frame has a horizontal lower leg that slides in a groove in said housing, and said horizontal leg contains an end termination for attachment of an extension link that can rotate, (d) said injector handle attached to the outside of said housing contains two contoured legs that straddle said housing, and each leg is attached to said pivot point in said housing, and said handle is shaped to provide finger or hand grips, and can rotate around said pivot that is retained by a capture pin, (e) said handle of extended length provides leverage for compressing said drive rod compression spring, containing said extension link that can rotate around said handle attachment point, and permits said link to rotate when said handle is rotated, and attached to said slide frame, it pivots about at the opposite end from said handle, so that when said handle is rotated down or up, said extension link pushes or pulls on said slide frame, (f) said slide frame movement in one direction pulls said drive rod to the latched position, with a connector link attached to the upright supports of said frame and on the opposite end is attached to a piston extension with a rod latch pivot pin, (g) said piston provides a vacuum for said injector when applied to the recipient's skin to pull the skin tight against suction ports in said ampule, and position said outlet orifice correctly for injection of medicament, and provides a vacuum seal to said ampule with the skin to prevent inadvertent triggering of said injector with the use of an interlock piston rod to engage or disengage said release catch, (h) said piston that contains an O-ring seal that ensures said piston can produce vacuum for actuation of said small interlock piston rod, and ensures said vacuum provided will position said interlock piston rod to engage said release arm, and either lock it in non-release, or release position, and said arm is torsion spring loaded to lock position and able to rotate to the two operating positions around a pivot pin that interfaces with said injector housing, (i) said release button installed in said injector housing that when pushed inward contacts said release arm and rotates it downward to lift said release catch that locks said compression spring in its compressed position, and said button is retained in said injector housing flush with the structure's outer surface to prevent operators from inadvertently pushing of said button down until required by the operating procedure and is retained in said structure with a retention snap ring, (j) said release catch contains said torsion spring that drives it into the lock position to hold said drive rod against said compression spring and contains an angular surface that provides for contact with said release arm during release function, and said release catch is pivoted around said pivot point provided by said latch pin that engages said housing, (k) a suction manifold system comprised of vacuum ports in said housing to receive vacuum pressure from said vacuum piston and conduct a vacuum through ported passages in said structure to said interlock piston chamber, and to said suction tubes that interface with said ampule, and said passages are sequentially opened and closed by positioning of said interlock piston and a pair of suction tubes conduct suction to said suction ports, in said ampule.

2. Said injector of claim 1 wherein is externally air pressurized for activating said vacuum and sequencing said injector components, (a) said injector contains a trigger assembly operated by the operator's finger for initiation and movement of a valve in the said injector that opens and blocks externally supplied air pressure to a return piston that is connected to a vacuum piston with a connecting rod, (b) said vacuum piston provides said vacuum for interlock functions of said release button and release catch to initiate injection of medicament, and said piston is moved by said return piston to create a vacuum at the interface contact surface of the recipient's skin and said ampule containing said medicament, (c) a small compressing spring installed between, said drive rod and said drive cylinder to ensure constant contact with said ampule plunger and prevent impact of said drive rod.

3. Said disposable filled ampule of claim 1, attached to said injector and contacts vacuum tubes, that engage a chamber for containing medicament, having an internal seal that captures medicament inside said chamber, (a) said ampule whose chamber is provided with gradient markers on the exterior surface to indicate the quantity of medicament within, and said chamber is contoured on its inner surface and contains a precision contoured throat to aid in acceleration of medicament injection by reduction of the fluid drag when said ampule receives an impact impulse from said spring loaded drive rod and increases the acceleration of said piston which results in a faster pressure rise and injection of medicament, and therefore, the medicament is driven out of said ampule with a known controlled impact impulse force, (b) said ampule contains said outlet orifice that is varied in location by varying the distance between the centerline of said orifice and the vacuum port plane, and can contain said intradermal, subcutaneous or intramuscular injection medicaments and horizontally inject them into predetermined depths in skin tissue layer, by controlling the dispersement of medicament, by varying the angle between the perpendicular to said orifice and the vacuum port level plane, (c) said ampule contains locking tabs on each end for engagement with said injector, in order to be correctly positioned and retained for engagement with said vacuum suction ports, and the interface surface is sealed with said suction ports, that engage recipient's skin and stretches the skin between said ports for medicament injection into the skin, (d) said ampule has provisions for filling with medicament from an external supply by either use of an adaptor assembly that holds and seals said ampule for filling medicament with a needle syringe through said injector's orifice, or filling through a stopper with provisions for insertion of a probe on a nozzle, that penetrates said stopper in said ampule, and whose said nozzle contains a shoulder that bears on said ampule's surface and automatically locates said probe correctly for medicament filling, after evacuating air from said ampule prior to filling of medicament and sealing of the passage evacuated, and then reinserting said probe on said nozzle through said stopper, and filling said ampule with medicament, (e) a means for plugging of said ampule orifice with a plug, when filling medicament, and said plug contains an enlarged head for installation and removal, with a capture pad to prevent it from being sucked into said orifice and from being driven out of said orifice, with the use of a protective outer doubler covering and all other openings of said ampule are protected with coverings to maintain full sterile conditions within said ampule, and provide for removal and disposal of said ampule orifice plug with the disposed said protective shield that contains a tab for easier removal of said shields from said ampule.

4. A process for a needle-free jet injection depositing a subcutaneous, intradermal or intramuscular injection of medicament into the tissue of a human or animal comprising the steps of;

(a) obtaining the injector as recited in claim 1, (b) injecting a premeasured dose of medicament, from said injector into the tissue of the human or animal subcutaneous, intradermal or intramuscular.

* * * * *